US007972334B2

(12) United States Patent
McGreevy et al.

(10) Patent No.: US 7,972,334 B2
(45) Date of Patent: Jul. 5, 2011

(54) COAPTIVE TISSUE FUSION METHOD AND APPARATUS WITH ENERGY DERIVATIVE PRECURSIVE ENERGY TERMINATION CONTROL

(75) Inventors: Francis T. McGreevy, Aurora, CO (US); Katherine R. Pavlovsky, Denver, CO (US); Alison Rogers, Seattle, WA (US)

(73) Assignee: ConMed Corporation, Uitca, NY (US)

( * ) Notice: Subject to any disclaimer, the term of this patent is extended or adjusted under 35 U.S.C. 154(b) by 891 days.

(21) Appl. No.: 11/974,721

(22) Filed: Oct. 16, 2007

(65) Prior Publication Data

US 2009/0182321 A1   Jul. 16, 2009

(51) Int. Cl.
*A61B 18/12* (2006.01)
(52) U.S. Cl. ............... 606/51; 606/32; 606/40; 606/33; 606/34
(58) Field of Classification Search .............. 606/32–35, 606/40, 50–52
See application file for complete search history.

(56) References Cited

U.S. PATENT DOCUMENTS

| 4,658,819 | A | 4/1987 | Harris et al. |
|---|---|---|---|
| 4,860,745 | A | 8/1989 | Farin et al. |
| 5,370,645 | A | 12/1994 | Klicek et al. |
| 5,403,312 | A | 4/1995 | Yates et al. |
| 5,422,567 | A | 6/1995 | Matsunaga |
| 5,437,664 | A | 8/1995 | Cohen et al. |
| 5,443,463 | A | 8/1995 | Stern et al. |
| 5,514,129 | A | 5/1996 | Smith |
| 5,540,684 | A | 7/1996 | Hassler, Jr. |
| 5,558,671 | A | 9/1996 | Yates |
| 5,599,344 | A | 2/1997 | Paterson |
| 5,720,744 | A | 2/1998 | Eggleston et al. |
| 5,817,093 | A | 10/1998 | Williamson, IV et al. |
| 5,827,271 | A | 10/1998 | Buysse et al. |
| 6,010,516 | A | 1/2000 | Hulka |
| 6,033,399 | A | 3/2000 | Gines |
| 6,083,223 | A | 7/2000 | Baker |
| 6,142,992 | A | 11/2000 | Cheng et al. |
| 6,203,541 | B1 | 3/2001 | Keppel |
| 6,210,403 | B1 | 4/2001 | Klicek |
| 6,228,080 | B1 | 5/2001 | Gines |
| 6,261,286 | B1 | 7/2001 | Goble et al. |
| 6,267,761 | B1 | 7/2001 | Ryan |
| 6,270,497 | B1 | 8/2001 | Sekino et al. |
| 6,358,246 | B1 | 3/2002 | Behl et al. |
| 6,398,779 | B1 | 6/2002 | Buysse et al. |

(Continued)

OTHER PUBLICATIONS

Physical Factors in Electrocoaptation of Blood Vessels. By Bernard Sigel and Fred L. Hathe, Arch Surg; vol. 95, p. 54-58, Jul. 1967.

(Continued)

*Primary Examiner* — Linda C Dvorak
*Assistant Examiner* — Amanda Scott
(74) *Attorney, Agent, or Firm* — John R. Ley

(57) ABSTRACT

Biological tissue is sealed or fused to occlude an opening by compressing apposite sidewall portions of the tissue and applying sufficient energy to cause the fibers of the compressed apposed sidewall portions to intertwine and fuse with one another to form a permanent seal. The energy application is controlled by detecting a precursor fusion condition while applying the energy and before sufficient energy has been applied to achieve a permanent seal. The application of energy is terminated in a time-delayed relationship to the detection of the precursor fusion condition. The precursor fusion condition is detected from derivative values of the total accumulated amount of high-frequency energy conducted through the tissue.

23 Claims, 6 Drawing Sheets

U.S. PATENT DOCUMENTS

| | | |
|---|---|---|
| 6,562,037 B2 | 5/2003 | Paton et al. |
| 6,733,498 B2 | 5/2004 | Paton et al. |
| 2003/0114845 A1 | 6/2003 | Paton et al. |
| 2004/0068304 A1 | 4/2004 | Paton et al. |
| 2007/0066969 A1* | 3/2007 | McGreevy et al. ............. 606/32 |

OTHER PUBLICATIONS

Electrosurgical Tissue Resection: A Numerical and Experimental Study. By Dmitriy E. Protsenko and John A. Pearce, Proceedings of SPIE vol. 4954, p. 64-70 (2003).

Evaluation of a Vessel Sealing System, Bipolar Electrosurgery, Harmonic Scalpel, Titanium Clips, Endoscopic Gastrointestinal Anastomosis Vascular Staples and Sutures for Arterial and Venous Ligation in a Porcine Model. By Landman, Kerbl, Rehman, Andreoni, Humphrey, Collyer, Olweny, Sundaram and Clayman. Journal of Urology, vol. 169, 697-700, Feb. 2003.

Automatically Controlled Bipolar Electrocoagulation—"Coa-Comp." By Bertil Vallfors and Bjorn Bergdahl. Neurosurg. Rev. 7, 187-189 (1984).

"Coa-Comp"—Computerized Automatic Bipolar Electrocoagulation for Neurosurgery and Precision Surgery. By Vallfors, B., Bergdahl, B. Acta Neurochirugica V. 66 n. 3/4 1982 p. 256.

\* cited by examiner

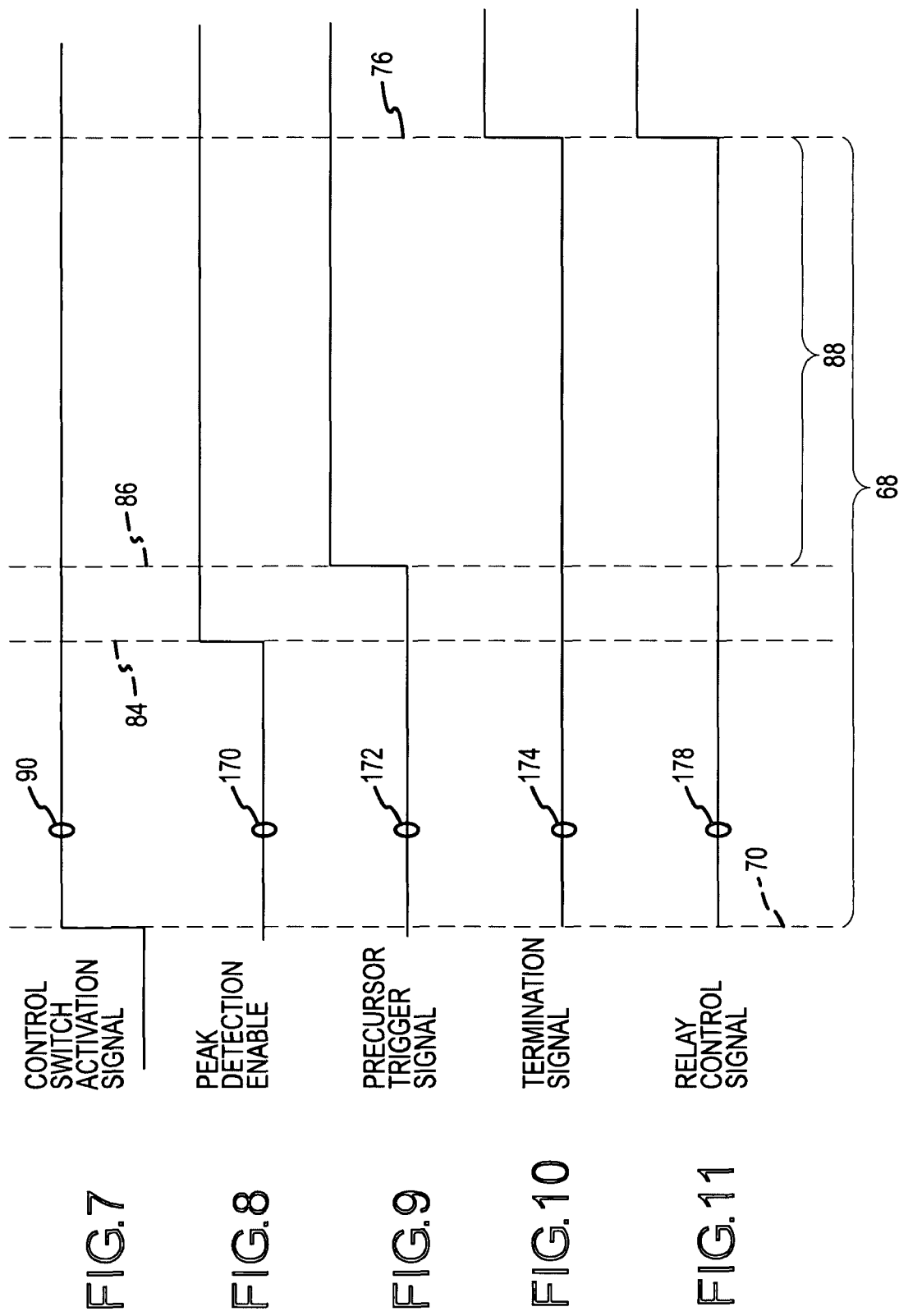

COAPTIVE TISSUE FUSION METHOD AND APPARATUS WITH ENERGY DERIVATIVE PRECURSIVE ENERGY TERMINATION CONTROL

The present invention relates to fusing or sealing biological tissue to permanently occlude a lumen, duct, passageway or chamber formed in and surrounded by the tissue. More particularly, the present invention relates to a new and improved coaptive sealing apparatus and method which terminate the delivery of energy to the tissue based on a precursive fusion condition that is based on a derivative of the energy delivered to the tissue.

BACKGROUND OF THE INVENTION

Tissue fusion has been used in medical procedures for many decades, primarily to prevent bleeding from severed blood vessels. One age-old technique of fusing tissue involves heat application to cauterize vessels. More recent techniques involve the application of electrosurgical electrical energy to tissue to create the heat necessary for tissue fusion. The electrical energy may be applied in a coagulative or a coaptive manner.

Coagulative tissue fusion involves applying electrosurgical energy to the open vessel. The heat created by the electrical energy shrinks and constricts the blood vessel, and blood coagulation contributes to occluding the vessel. Generally speaking, coagulative tissue fusion is primarily useful on relatively small vessels. In electrosurgery, coagulative tissue fusion occurs during standard coagulation and spray coagulation. Coagulative tissue fusion on larger vessels is regarded as less reliable, and therefore poses more risks of internal bleeding after the surgery has been completed. For this and other reasons, coaptive electrosurgical tissue fusion, or some other type of tissue sealing and closure technique, such as mechanical ligature, is generally regarded as more favorable and reliable for larger vessels.

Coaptive electrosurgical tissue fusion involves physical apposition and compression of the tissue which surrounds the lumen, duct, passageway or chamber to be sealed, followed by heating the compressed apposed tissue portions. Usually the source of heat is electrical energy, which is either conducted through the tissue or is conducted through a heating element that is placed in contact with the tissue. One well-known and relatively old technique of coaptive electrosurgical tissue fusion involves grasping the vessel with a hemostat (a scissors-like clamping device) and conducting electrosurgical energy through the hemostat to the tissue. More recent coaptive electrosurgical tissue fusion devices use a specifically-configured handpiece with jaws that clamp around and compress the vessel while a controlled and regulated amount of electrical current is applied to electrodes within the jaws to heat the tissue. Radio frequency (RF) energy is used primarily to create the heating effects because the tissue conducts the current, and RF currents minimally stimulate the nervous system, if at all. Other known sources of heating energy include direct current (DC) applied to resistive heating elements, ultrasound which vibrates the tissue to generate heat, microwaves which interact with the molecular structure of the tissue to generate heat, and light which transfers energy to the cellular components of the tissue, among others.

In coaptive tissue fusion, it is very important to control the amount of energy delivered to the tissue to achieve an effective seal or fusion of the tissue. An effective seal is one which prevents leaks caused by blood pressure and other stresses and pressures from the fluid within the occluded lumen, duct, passageway or chamber. Applying too much energy to the tissue may destroy or denature the tissue to the point where collagen and elastin fibers within the tissue are incapable of fusing and intertwining in such a way to achieve an effective seal. Intertwining and fusing the fibers within the tissue of the two apposite tissue portions is believed to be the primary mechanism for fusing and sealing the tissue. Applying too much energy may obliterate the tissue or destroy or compromise the ability of the fibers to loosen and unwind and thereafter tangle, intertwine and fuse to join the previously separate apposed tissues in a single tissue mass. Applying too little energy to the tissue will not increase the flexibility of the fibers to the point where they will loosen enough to interact and fuse sufficiently with the fibers of the apposite tissue.

In those prior art tissue sealing devices such as the hemostat, the application of the electrical energy to the tissue is not specifically controlled but is instead left to the surgeon to determine when enough heat has been applied. Determining when enough heat energy has been applied is particularly difficult if not impossible, because different tissues respond differently. Determining whether a seal is effective by simple observation is impossible. Therefore, most modern coaptive tissue sealing devices attempt to control the application of energy automatically to achieve an effective seal.

Modern coaptive tissue sealing devices typically use complex functional components for measuring and calculating tissue impedance, tissue temperature and other physical tissue parameters to determine and control the amount of energy applied. Most of these devices include feedback control loops which depend on the values of these tissue parameters to adjust the energy delivered to the tissue. In most cases, these tissue parameters are calculated based on measurements of the voltage and current applied to the tissue. Calculations based on the measurements of the voltage and current must thereafter be performed, and the calculated values used in the feedback control loops and other power delivery functionality of the devices. The capability of such prior art tissue sealing devices is therefore subject to a number of complex constraints, including the accuracy of sensing the values and the tissue parameters, the speed and reliability of making the calculations, and the ability of the components of the device to respond. Consequently, most modern coaptive tissue sealing devices are relatively complex in their functionality and relatively expensive because of their complex functionality.

Examples of these types of prior art tissue sealing devices are those which respond to a measured, fixed or variable impedance level occurring while heating the tissue to indicate that the seal is complete. Upon achieving this impedance level, the delivery of electrical energy to the tissue is terminated. Detecting impedance can be computationally intensive and time consuming, thereby delaying the calculated value of the tissue impedance relative to the actual value of the tissue impedance at the time that the calculation is made available. Detecting impedance can be virtually impossible under conditions where the electrical energy is arcing between the jaws which grasp the tissue. Arcing at the ending stages of the tissue sealing process is prevalent in prior art RF tissue sealing devices. Consequently, using an impedance value to establish the point for terminating the delivery of RF electrical energy to the tissue makes it very difficult or impossible to achieve optimum sealing conditions.

Other types of prior art tissue sealing devices determine the impedance level while modulating the electrical energy delivered to the tissue. Modulating the electrical energy delivered is intended to prevent overheating of the tissue, and in that sense is an implicit recognition of the slow response of the feedback control system in regulating the output energy delivered to the tissue. Moreover, modulating the electrical energy delivered while simultaneously calculating impedance and other control parameters increases the complexity of the equipment required.

Still other types of prior art tissue sealing devices automatically reduce the electrosurgical power delivered throughout the tissue sealing event to reduce tissue charring, and then terminate the energy delivery when the current drops below a certain level. Reducing the energy delivery rate extends the time required to achieve an adequate seal, and may therefore result in greater thermal damage to the tissue because of the prolonged heat application time.

Because of the variable and uncertain effects from most prior art tissue sealing devices, surgeons are frequently prone to perform multiple seals on the same vessel in an attempt to assure that one of these seals will be effective. Performing multiple seals on the same vessel is time-consuming. The number of seals necessary to be performed in a surgical operation can vary according to the type of operation, but the use of a tissue sealing device in surgery usually occurs under circumstances where the surgeon has judged that the procedure will be more efficiently performed by using a tissue sealing device compared to using an alternative tissue sealing technique such as mechanical ligature. Accordingly and in addition to the requirement for permanent and leak-free seals, the speed at which the tissue sealing device accomplishes the seal is very important. Minimizing the time required to achieve effective seals diminishes the time of the surgical procedure and therefore minimizes risks associated with the procedure.

SUMMARY OF THE INVENTION

The present invention fuses and seals tissue by determining a straightforward precursor fusion condition during the progress of a tissue sealing cycle. The precursor fusion condition establishes the conditions for terminating the delivery of electrical energy. The precursor fusion condition is relatively easily sensed and determined, and the precursor condition is used in a straightforward manner to control energy application without requiring complex calculations, feedback power control loops, or energy modulation techniques. Furthermore, even though the precursor fusion condition is not predictably and reliably related to tissue impedance, the precursor fusion condition nevertheless predicts conditions under which a very effective seal is achieved in different types of tissues. The present invention permits a prior art electrosurgical generator and a prior art tissue sealing handpiece to be used together as a tissue fusion apparatus, thereby avoiding the necessity of using a separate and expensive energy generator designed specifically for tissue sealing purposes. Effective tissue seals are obtained in considerably shorter times.

The present invention involves a method, a tissue sealing apparatus, and a controller, each of which is used to coaptively seal a sidewall of biological tissue which surrounds and defines an opening in the tissue to occlude the opening. The tissue of the sidewall includes biological fibers. Portions of the sidewall are compressed in apposition to one another to occlude the opening, preferably by the use of a conventional tissue sealing handpiece having jaws which close on the tissue. Sufficient energy to heat the tissue is applied to the compressed apposed sidewall portions to cause the fibers of the compressed apposed sidewall portions to intertwine and fuse with one another to a sufficient degree to hold the apposed sidewall portions permanently together and occlude the opening permanently. A precursor fusion condition is detected while the energy is applied but before sufficient energy has been applied to cause the fibers to intertwine and fuse sufficiently for permanently occluding the opening. Thereafter, the application of energy is terminated in a time delayed relationship to the detection of the precursor condition when the sufficient degree of energy has been conducted to the compressed apposed sidewall portions. The fibers of the apposed sidewall portions intertwine and fuse with one another sufficiently to hold the apposed sidewall portions permanently together and permanently occlude the opening.

In the method aspect of the present invention, the precursor fusion condition is determined by establishing an energy signal related to the cumulative radio frequency (RF) energy conducted through the compressed apposite sidewall portions during the tissue sealing cycle, and then mathematically differentiating the energy signal to obtain derivative values related to the rate of change of the energy signal or energy delivered while the RF energy is applied. The precursor fusion condition is determined from the derivative values, preferably at the peak value of the second derivative of the cumulative delivered energy. The application of energy is terminated in a time-delayed relationship to the detection of the precursor fusion condition, at a point when sufficient energy has been conducted to the compressed apposed sidewall portions.

In the tissue sealing apparatus aspect of the present invention, a handpiece, an electrical energy generator and a controller are employed. The handpiece has jaws that close on and compress the sidewall portions to occlude the opening. The generator delivers high frequency energy to the jaws. The controller controls the delivery of the high frequency energy from the generator to the jaws.

In the controller aspect of the present invention, the controller is used in combination with a conventional electrosurgical generator and conventional handpiece to create and obtain an effective tissue fusion device.

The controller, which is also used in the tissue sealing apparatus, includes a switch, a precursor detector and an energy completion timer. The switch controls the delivery of high frequency or RF energy from the generator to the jaws. In a closed position, the switch conducts energy from the generator to the jaws. In an opened position, the switch terminates the conduction of energy to the jaws. The precursor detector senses the high frequency or RF energy conducted from the generator through the switch to the jaws, establishes an energy signal related to the cumulative high frequency energy delivered to the tissue during the tissue sealing cycle, and mathematically differentiates the energy signal to establish derivative values. The precursor detector determines the precursor fusion condition from the derivative values, preferably at the maximum peak of the derivative values, and delivers a precursor trigger signal upon detecting the precursor fusion condition. The precursor trigger signal causes the energy completion timer to assert a control signal to the switch at a time after the precursor fusion condition has been detected to open the switch after sufficient energy has been applied to hold the apposed sidewall portions permanently together and occlude the opening permanently.

More specific aspects of the invention include terminating the application of energy after the expiration of a fixed time duration after detecting the precursor fusion condition, detecting the precursor fusion condition at a peak value of the derivative values, and comparing the derivative values to a predetermined threshold value as a condition of detecting the precursor condition, among other things. Typically, the energy completion time is in the range of 0.8 to 1.2 seconds after detection of the precursor fusion condition.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

BRIEF DESCRIPTION OF THE DRAWINGS

FIGS. 7-11 are waveform diagrams having a common time reference which illustrate certain signals present in the controller shown in FIG. 6.

DETAILED DESCRIPTION

Figure 1:
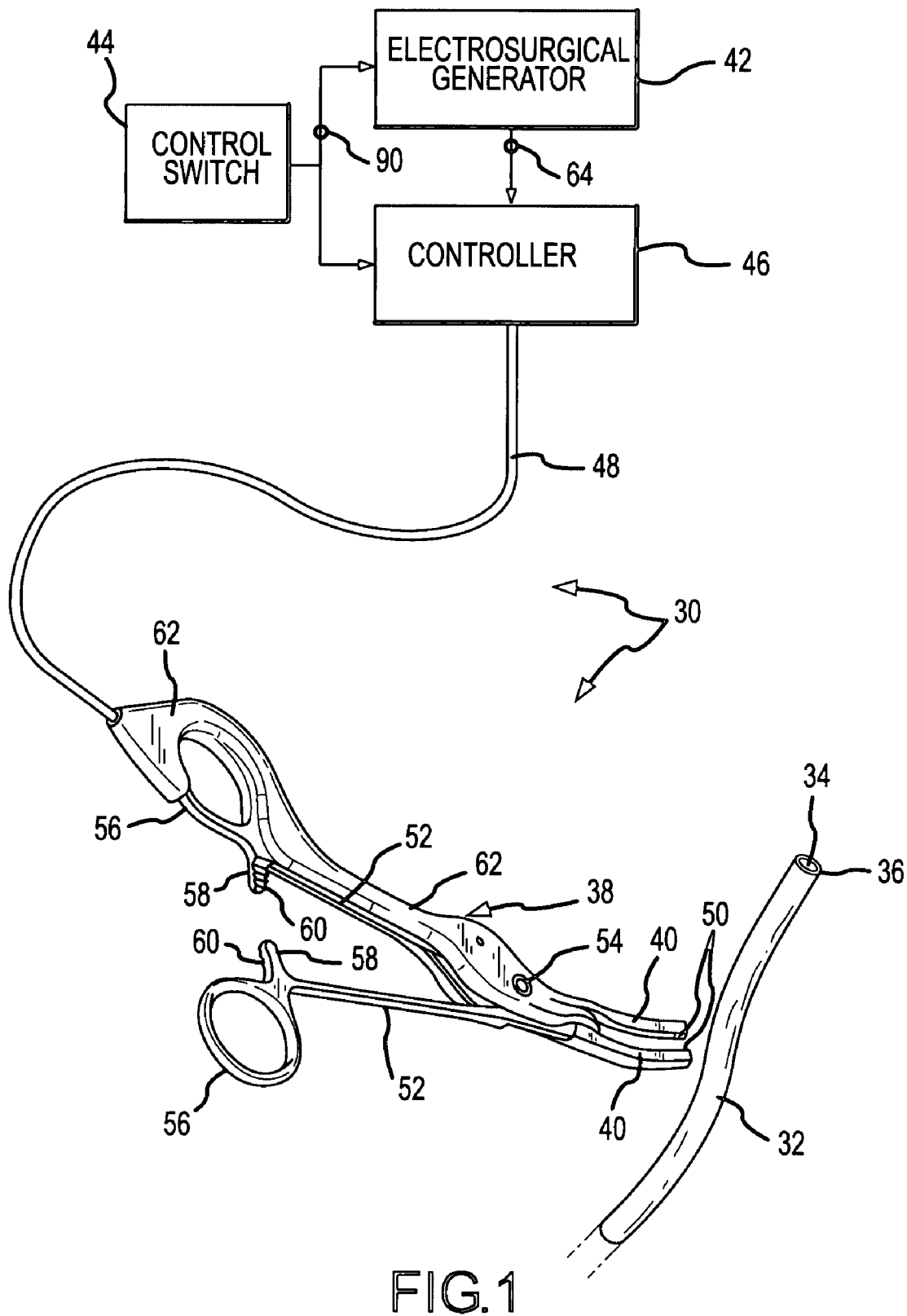
FIG. 1 is an illustration of a coaptive biological tissue sealing apparatus embodying the present invention, along with a portion of a biological vessel on which a tissue sealing treatment cycle is performed.
Figure 2:
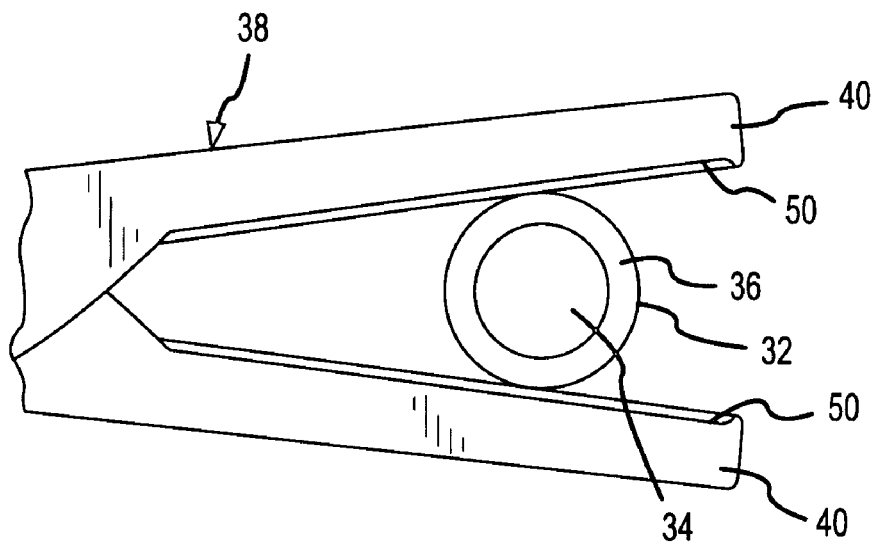
FIG. 2 is an enlarged partial side elevational view of jaws of a handpiece of the apparatus shown in FIG. 1, illustrating the jaws on either side of a vessel shown in cross-section before commencing the tissue sealing treatment cycle.

A coaptive biological tissue sealing apparatus 30, the use of which also exemplifies the practice of a method of coaptively sealing biological tissue, both of which incorporate the present invention, is shown in FIG. 1. The coaptive tissue sealing apparatus 30 is used to permanently close a lumen, duct, passageway or chamber formed in and surrounded by the biological tissue. The biological tissue is exemplified in FIG. 1 (and in FIGS. 2-4) by a biological vessel 32, such as an artery or vein. Other examples of biological tissue which may be permanently sealed by use of the present invention include fallopian tubes, bile ducts, tissue surrounding an alveoli or air sac in the lung, the colon or bowel, and any other tissue structure where ligation might otherwise be performed.

For the present purposes of describing preferred embodiments of the sealing apparatus 30 and the coaptive sealing method which incorporate the present invention, the vessel 32 will be used as an example of the biological tissue which is sealed, and a lumen 34 in the vessel 32 will exemplify the lumen, duct, passageway or chamber which is to be permanently occluded by sealing the biological tissue. The biological tissue of the vessel 32 is represented by a sidewall 36 of the vessel 32. The lumen, duct, passageway or chamber in the biological tissue will be referred to generically as an "opening" in the context of the following appended claims which define the invention, although this detailed description of the preferred embodiments may also occasionally refer to an "opening" in the same generic context. That portion of the biological tissue which surrounds and defines the "opening" will be referred to as a "sidewall" in the context of the following appended claims which define the invention, and throughout this detailed description of the preferred embodiments, since the vessel 32 is defined by its sidewall 36. Therefore, in accordance with this naming convention, the sidewall 36 of the vessel 32 as used in the following detailed description is one example of "sidewall" of the biological tissue which is sealed, and the lumen 34 of the vessel 32 is one example of an "opening" which may be permanently occluded or closed by sealing the apposite portion of the "sidewall" of the biological tissue which initially defined and surrounded the "opening."

A handpiece 38 of the apparatus 30 is manipulated by a surgeon or medical personnel to grip the vessel 32 or other tissue between jaws 40 of the handpiece 38 and compress opposite portions of the sidewall 36 of the vessel 32 in apposition with one another to occlude the lumen 34 through the vessel 32 and to force the apposed sidewall portions 36 into a diminished thickness compared to their natural thickness. Thereafter an electrosurgical generator (ESG) 42 is activated to deliver electrosurgical current to the compressed apposite portions of the vessel sidewall 36. The electrosurgical energy or current delivered by the electrosurgical generator 42 in accordance with the present invention is typically bipolar radio frequency (RF) electrosurgical current. The energy is delivered from the electrosurgical generator 42 in response to closing or otherwise activating a control switch 44, such as a conventional ESG foot switch. The electrosurgical current is conducted through a controller 46 and through conductors 47 (FIG. 6) of a cable 48 to the jaws 40 of the handpiece 38. The jaws 40 include electrodes 50 for conducting the electrosurgical energy through the compressed apposite portions of the sidewall 36 of the vessel 32.

The electrical current is conducted through the compressed apposite portions of the vessel sidewall 36 and heats those sidewall portions. The compressed apposite sidewall portions are permanently fused or sealed together as a result of the mechanical compression force and the heat created by the electrical current conducted through the sidewall portions. The fusion of the apposite sidewall portions permanently occludes the lumen 34 through the vessel 32, thereby preventing fluid which is normally conducted through the lumen 34 from leaking through the occlusion and from the vessel 32.

Reliably and permanently occluding the vessel 32 is very important in surgery. In the case of the vessel 32 being an artery or a vein, the permanent occlusion prevents blood loss during the surgical procedure and after the procedure has been completed and any incision in the patient has been closed. In the case of lung tissue, sealing the alveoli permits the lung to function as an air-tight enclosure which is necessary for effective respiration. The integrity of the occlusion is sufficient to withstand the high end of expected or normal range of pressures of the fluid within the biological tissue. In the case of an artery or a vein, that normal range of pressures will be the systolic and diastolic blood pressure. Typically, the seal created by the present invention will have sufficient integrity to withstand ruptures from a range of fluid pressures which is considerably greater than the normal range of pressures experienced by the biological tissue which defines the lumen or opening within the vessel.

The technique for fusing or sealing biological tissue is relatively well-known. The application of the heat energy combined with sufficient compression of the apposed sidewall portions of the vessel 32 first loosens or denatures the natural intertwined or cross-linked fibers within the tissue, principally collagen and elastin fibers. Loosening the natural physical structure of these fibers makes them more malleable or flexible and allows them to fuse and reform into another different intertwined physical structure with other fibers while cooling. The compression of the tissue while the fibers are loosened and flexible allows the fibers of the apposed sidewall portions to intertwine with one another, thereby permanently creating a fused intertwined physical structure of those fibers, and this fused intertwined physical structure permanently seals the apposed sidewall portions together into the permanent occlusion of the lumen 34 or opening.

A number of factors can influence the strength and integrity of the occlusion. If the compression of the sidewall portions is insufficient, the fibers will not be sufficiently close or proximal to one another to create enough intertwining and fusion to hold the tissue portions together. In general, the necessity to apply sufficient compression to the sidewalls of the tissues has been recognized as a necessity to achieve adequate sealing or fusion of the biological tissue. Compressing the sidewall 36 is accomplished by use of the handpiece 38.

Figure 3:
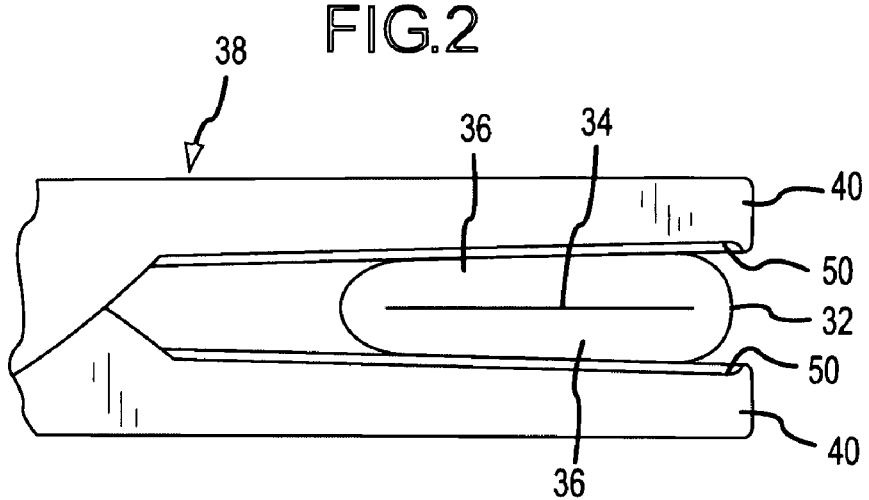
FIG. 3 is a side elevational view of the jaws shown in FIG. 2, illustrating compressing the vessel during the tissue sealing treatment cycle.

Although the handpiece 38 may assume different forms, the type of handpiece 38 shown in FIG. 1 includes two arms 52 which are pivotally connected together at a middle pivot point 54 to locate the jaws 40 on the distal ends of the arms 52. Finger enclosures 56 are formed on the opposite ends of the arms 52 from the jaws 40. Squeezing the finger enclosures 56 toward one another pivots the arms 52 about the pivot point 54 and moves the jaws 40 toward one another from an open position surrounding the vessel 32, shown in FIG. 2. Further movement of the finger enclosures 56 toward one another causes the jaws 40 to compress the sidewall 36 and close the lumen 34, as shown in FIG. 3. In the state shown in FIG. 3, the opposite portions of the sidewall 36 have contacted one another in apposition and completely close the lumen 34. The relative thickness of the apposite portions of the sidewall 36 has compressed somewhat to the limit of the force applied from the jaws 40 against the unheated sidewalls 36 of the vessel 32.

The resistance of compressing the apposite portions of the sidewall 36 causes the arms 52 to deflect toward one another along their longitudinal extension. Tabs 58 extend toward one another near the proximal end of the arms 52 on the opposite side of the arms 52 from the finger enclosures 56 (FIG. 1). The tabs 58 include teeth 60 which extend from the tabs 58 in a mutually facing relationship. The teeth 60 selectively engage one another and disengage from one another when the proximal ends of the arms 32 move close to one another as a result of finger pressure applied by squeezing the finger enclosures 56. The teeth 60 engage one another in a ratchet-like or detent-like manner to maintain the compressive force on the apposite portions of the sidewall 36. In this manner, the user is not required to maintain the compressive force on the apposite sidewall portions. The teeth 60 of the tabs 58 remain engaged with one another while the sidewall 36 of the vessel 32 is heated. The electrical current is conducted through the compressed apposite sidewalls 36 as shown in FIG. 3.

As the compressed apposite sidewall portions are heated by the electrical current, the tissue structure of the sidewall 36 collapses to reduce the resistance created by compression of the tissue between the jaws 40. The jaws 40 move slightly closer to one another as a result of the tissue collapse. Some of the resistance force caused by the initial compression of the tissue between the jaws 40 is diminished, causing the amount of deflection of the arms 52 to be slightly reduced. However, the reduction in the amount of resistance after tissue collapse is not enough to completely eliminate any tissue resistance from the heated and compressed apposite portions of the sidewall 36, and therefore the resistance still maintains the teeth 60 of the tabs 58 of the handpiece engaged together. The continued engagement ensures that pressure is continuously applied to the apposite compressed portions of the sidewall 36 until the handpiece 38 is removed from the sealed vessel 32. To remove the handpiece 38, the teeth 60 of the tabs 58 are disengaged from one another by deflecting the arms 52 to separate the tabs 58 from one another, thereby releasing the vessel 32 from the jaws 40.

The electrodes 50 are positioned on the jaws 40 and are electrically insulated from the jaws to conduct the electrical current between one another and through the apposite compressed portions of the sidewall 36. In one type of handpiece 38, the electrodes 50 are part of a disposable assembly which is connected to at least one of the arms 52 and to both jaws 40. The electrodes 50 conduct the bipolar electrical energy as a result of connecting the electrode 50 on one jaw 40 to one pole of the RF bipolar electrical energy and connecting the electrode 50 on the other jaw 40 to conduct the other pole of the RF bipolar electrical energy. The two poles of bipolar electrical energy are conducted through separate conductors within the cable 48 and through an enclosure 62, which is attached to one of the arms 52 and which is part of the disposable assembly, to the electrodes 50 on the jaws 40.

Figure 4:
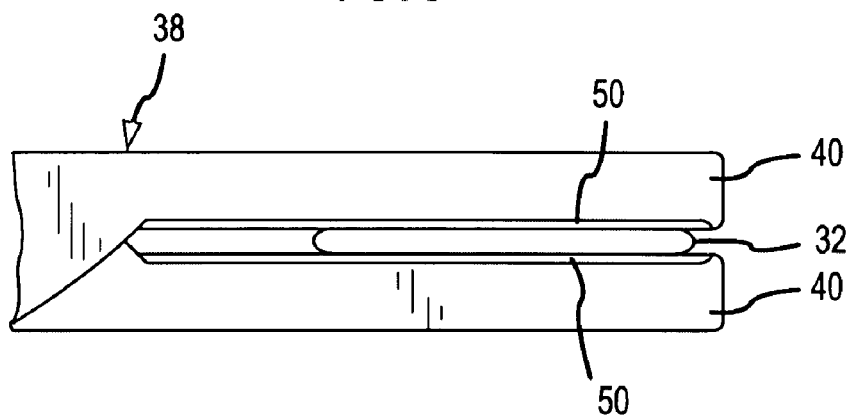
FIG. 4 is a side elevational view of the jaws shown in FIGS. 2 and 3, illustrating complete closure of the jaws on the vessel during the tissue sealing treatment cycle.

Since the electrodes 50 are connected to electrically opposite poles of the output energy from the electrosurgical generator 42, it is important that the electrodes 50 are not allowed to contact one another. Such contact would result in short-circuiting the bipolar electrosurgical energy delivered from the electrosurgical generator 42 and might damage the generator 42. To prevent the electrodes 50 from contacting one another, the mechanical structure of the handpiece 38 prevents the jaws 40 from completely closing into contact with one another as the tissue is heated as shown in FIG. 4. Instead, the jaws 40 stop moving toward one another at a position which creates a relatively narrow and uniform width gap of about 0.1 mm between the jaws 40. Fixing the gap between the jaws 40 in this manner also prevents the jaws 40 from mechanically severing the vessel 32 as a result of energy or pressure applied during tissue fusion.

The parallel facing relationship of the jaws 40 also creates a relatively uniform thickness of apposite compressed portions of the sidewall 36 between the electrodes 50. The uniform thickness of the apposite compressed sidewall portions provides a relatively uniform and equally distributed electrical load for conducting the electrical energy uniformly between electrodes 40 and through the compressed apposite sidewall portions of the vessel 32. The relatively uniform load distributes the electrical energy uniformly across the lateral dimension of the apposite compressed sidewall portions, thereby assuring that the amount of heating is approximately uniform in the lateral sense across the compressed apposite sidewall portions. Uniform distribution of the electrical energy is important to prevent some locations of the compressed apposite sidewall portions from becoming too hot and permanently and adversely influencing the ability of the tissue fibers to fuse and intertwine while leaving other locations of the compressed apposite sidewall portions without enough heat to adequately fuse and intertwine the fibers in those locations. The uniform energy distribution assures that all locations along the lateral width of the compressed apposite sidewall portions are heated approximately to the same extent at approximately the same time to achieve effective tissue fusion.

Another factor which can influence the strength and integrity of the tissue fusion is the amount and characteristics of the energy applied to heat and otherwise influence the fusing and intertwining characteristics of the fibers in the tissue. The application of the energy for heating the tissue is particularly important because it is more difficult to control compared to the compression of the tissue. Compression of the tissue, as described in conjunction with FIGS. 3 and 4, is relatively consistently obtained due to the mechanical nature of the handpiece and its ability to compress the apposite sidewall portions to approximately the same extent. If insufficient heat is applied, the fibers will not loosen sufficiently to reform in a fused and intertwined manner. If excessive heat is applied, the fibers are adversely affected to the point that they do not fuse and intertwine in the best effective manner. When RF electrosurgical energy is used for tissue fusion, applying the additional energy necessary to achieve adequate tissue fusion will generally result in the generation of arcs of the RF energy. The arcs have the tendency to penetrate into the tissue and may weaken the sidewall adjacent to the fused apposite sidewall portions, thereby diminishing the strength of the sidewall and creating the possibility of fluid leaks at the sealed location or at locations adjacent to the sealed location. It is therefore important to control the amount of energy applied to the tissue to achieve the best seal and to avoid the problems associated with inadequate and excessive energy and heat application.

The controller 46 controls the amount of energy applied to the tissue to obtain the best seal. The functionality of the controller 46 is based on the discovery that the energy application for tissue sealing is controlled very advantageously in relation to a precursor fusion condition, and that precursor fusion condition is determined by the peak value of a second derivative of a cumulative energy curve representative of the cumulative energy delivered to the tissue, as is described in greater detail below. After the occurrence of this precursor fusion condition, it is necessary to deliver additional energy to the tissue to obtain an effective seal. Terminating the delivery of electrosurgical energy at the moment when the precursor fusion condition exists has been shown not to result in an effective seal. In other words, terminating the application of heating energy when the precursor fusion condition occurs results in an insufficient number of collagen and elastin tissue fibers having loosened adequately enough to intertwine and fuse with one another. The additional energy is believed to be necessary to obtain the loosening, fusing and intertwining of the relatively high denaturing-temperature collagen and elastin fibers within the tissue.

The additional energy added after the occurrence of the precursor fusion condition must be sufficient to drive off a substantial portion of the intracellular fluid within the cells of the tissue. Removing the intracellular fluid is believed to create the beneficial effect of locating tissue fibers within sufficiently close physical proximity to fuse and intertwine without the intracellular fluid interfering with the fusion and intertwining. Eliminating a substantial portion of the intracellular fluid is accomplished by delivering enough additional energy to vaporize the intracellular fluid. Typically the intracellular fluid is predominantly water. Consequently, the temperature of the intracellular fluid must be raised to or above 100° Celsius in order to vaporize that intracellular fluid.

The controller 46 monitors characteristics of energy delivered from the electrosurgical generator 42 and conducted through the compressed tissue to determine the existence of the precursor fusion condition. The controller then permits the continued delivery of the additional electrical energy for a predetermined time sufficient to achieve effective tissue fusion before terminating delivery of electrical energy to the tissue. When the delivery of electrosurgical energy is terminated, the heated and compressed apposite sidewall portions cool to complete the fusion of the tissue.

Figure 5A:
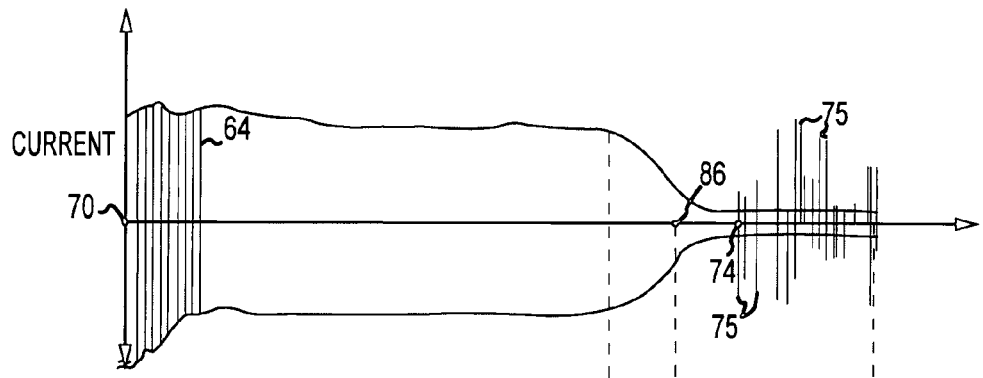
FIGS. 5a, 5b, and 5c are graphs on common time axes of exemplary waveform diagrams respectively showing current, voltage, cumulative energy and the second derivative of the cumulative energy applied to the vessel by the apparatus shown in FIG. 1, with FIG. 5c superimposed upon one another.
Figure 5B:
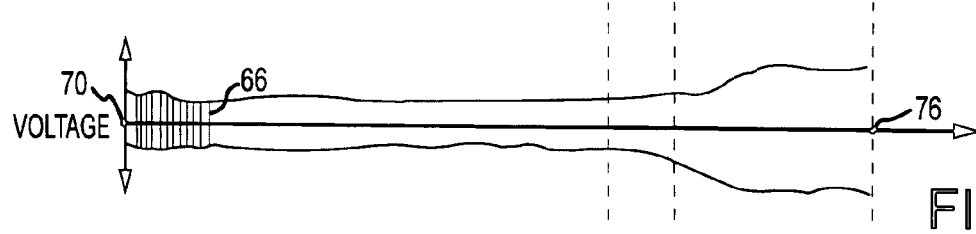
Figure 5C:
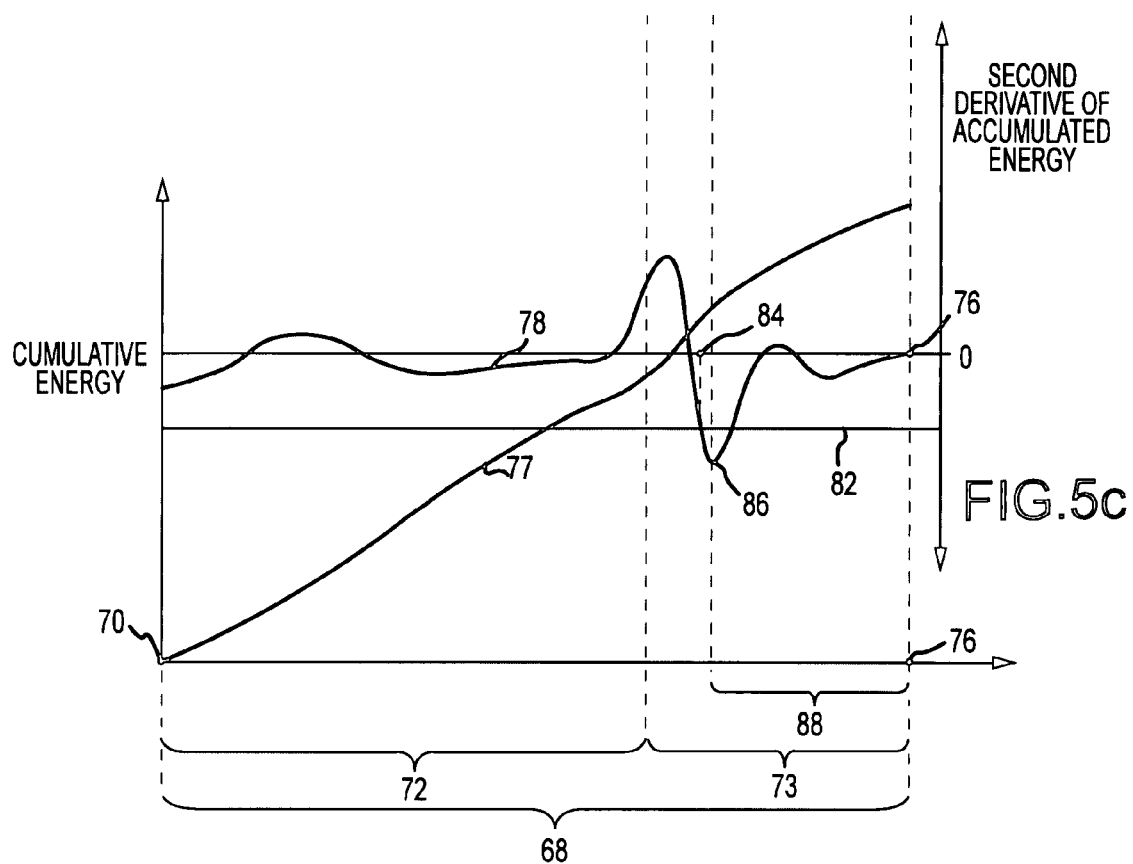

The characteristics of the energy delivered which is monitored by the controller 46 is understood by further reference to FIGS. 5a, 5b and 5c. An RF current 64 (FIG. 5a) is delivered at a voltage 66 (FIG. 5b) from the electrosurgical generator 42 (FIG. 1) and is conducted through the compressed apposite portions of the sidewall 36 (FIG. 4) during a single tissue sealing treatment cycle 68 in which tissue fusion or sealing is achieved. The treatment cycle 68 begins with an initial delivery of the RF current 64 at the voltage 66 from the electrosurgical generator 42 (FIG. 1) at cycle starting time point 70. The cycle starting time point begins an initial heating phase 72 of the treatment cycle 68. During the initial heating phase 72, the peak values of the RF current 64 delivered to the compressed apposite sidewall portions are somewhat constant as shown in FIG. 5a. The voltage 66 during the initial heating phase 72 also remains somewhat constant as shown in FIG. 5b.

The peak values of the RF current 64, the amount of the RF current 64, and the voltage 66 delivered during the initial heating phase 72 are dependent primarily on the capability of the electrosurgical generator to deliver power into relatively low resistance or impedance tissue. The RF current 64 and voltage 66 heats the compressed apposite portions of the sidewall 36 of the vessel 32 (FIG. 4). The temperature of the compressed apposite sidewall portions increases. The temperature is generally related to the cumulative amount of energy delivered to the tissue during the initial heating phase 72. The temperature increases somewhat linearly during the initial heating phase 72 as a result of the somewhat linear amount of energy delivered to and accumulated within the tissue as shown at 77 in FIG. 5c.

After the initial heating phase 72, the peak values of the cycles of the RF current 64 decrease during a current reduction phase 73 of the treatment cycle 68, primarily as a result of desiccation of the tissue resulting from vaporization of the intracellular fluid. During the current reduction phase 73 the voltage 66 initially remains approximately constant, but then increases as the desiccation continues. The impedance of the tissue increases to a point where the voltage 66 begins to increase and arcing may commence, beginning at time point 74. The arcs are illustrated by the relatively high-amplitude and short time duration spikes 75 in the RF current 64, in both the positive and negative directions, at and after time point 74. Although the arcing which commences at point 74 causes microscopic tissue destruction and weakening due to the arcs impacting or penetrating into the tissue, which raises the potential for compromising the integrity of the sealed tissue, such arcing is nevertheless necessary to apply the additional energy to the compressed apposite sidewall portions to create an adequate seal. An important aspect of the present invention is that only that amount of additional energy necessary for a good seal is applied. As a result, the amount of arcing which occurs is limited to the amount necessary to transfer enough energy to obtain the good seal, thereby minimizing the weakening of the tissue due to excessive arcing. Thereafter, the controller 46 (FIG. 1) terminates the delivery of electrical energy to the vessel 32 (FIG. 4) at the termination of the treatment cycle 68 at time point 76.

The precursor fusion condition is typically determined during the initial portion of the current reduction phase 73 of the treatment cycle 68. To determine the precursor fusion condition, the controller 46 (FIG. 1) creates a curve 77 which defines the total or cumulative energy delivered since the beginning of the tissue sealing cycle 68, as shown in FIG. 5c, and thereafter calculates the second derivative of the accumulated energy, as shown by curve 78 in FIG. 5c. When the values of the second derivative illustrated by curve 78 exceed a predetermined threshold value 82 (in the negative sense shown in FIG. 5c), at time point 84, the peak value of the second derivative curve 78 is thereafter determined. The peak value of the second derivative curve 78 is negative as shown in FIG. 5c and occurs at time point 86. The detection of the peak value of the second derivative curve 78 at time point 86 is the precursor fusion condition. From the precursor condition at point 86, the controller 46 (FIG. 1) counts a predetermined amount of time 88, during which the RF current 64 and the RF voltage 66 from the electrosurgical generator 42 (FIG. 1) continue to be delivered to the vessel 32 (FIG. 1) and cause the tissue to accumulate further energy shown by curve 77. The amount of time 88 is the energy completion time required to achieve tissue fusion. At the conclusion of the energy completion time 88, the controller 46 (FIG. 1) terminates the delivery of electrosurgical energy to the vessel 32 (FIG. 1) thereby ending the treatment cycle 68 at time point 76.

The termination time point 76 is not fixed relative to the starting time point 70, but is fixed relative to the occurrence of the precursor fusion condition at time point 86. Thus, during the energy completion time 88 between the time points 86 and 76, the additional amount of energy is delivered from the electrosurgical generator 42 (FIG. 1) to the tissue and that energy is necessary to assure effective tissue fusion. After the delivery of electrosurgical energy is terminated, the heated and compressed apposite sidewall portions cool, to complete the fusion of the tissue, and the handpiece 38 is removed from the vessel 32 (FIG. 1). If desired, the vessel 32 (FIG. 1) can then be severed at or adjacent to the fused apposed sidewall portions. In some circumstances, two seals at fusion locations which are longitudinally displaced along the vessel 32 (FIG. 1) may be created, so that the vessel can be severed between those two seals or fusion locations.

Figure 6:
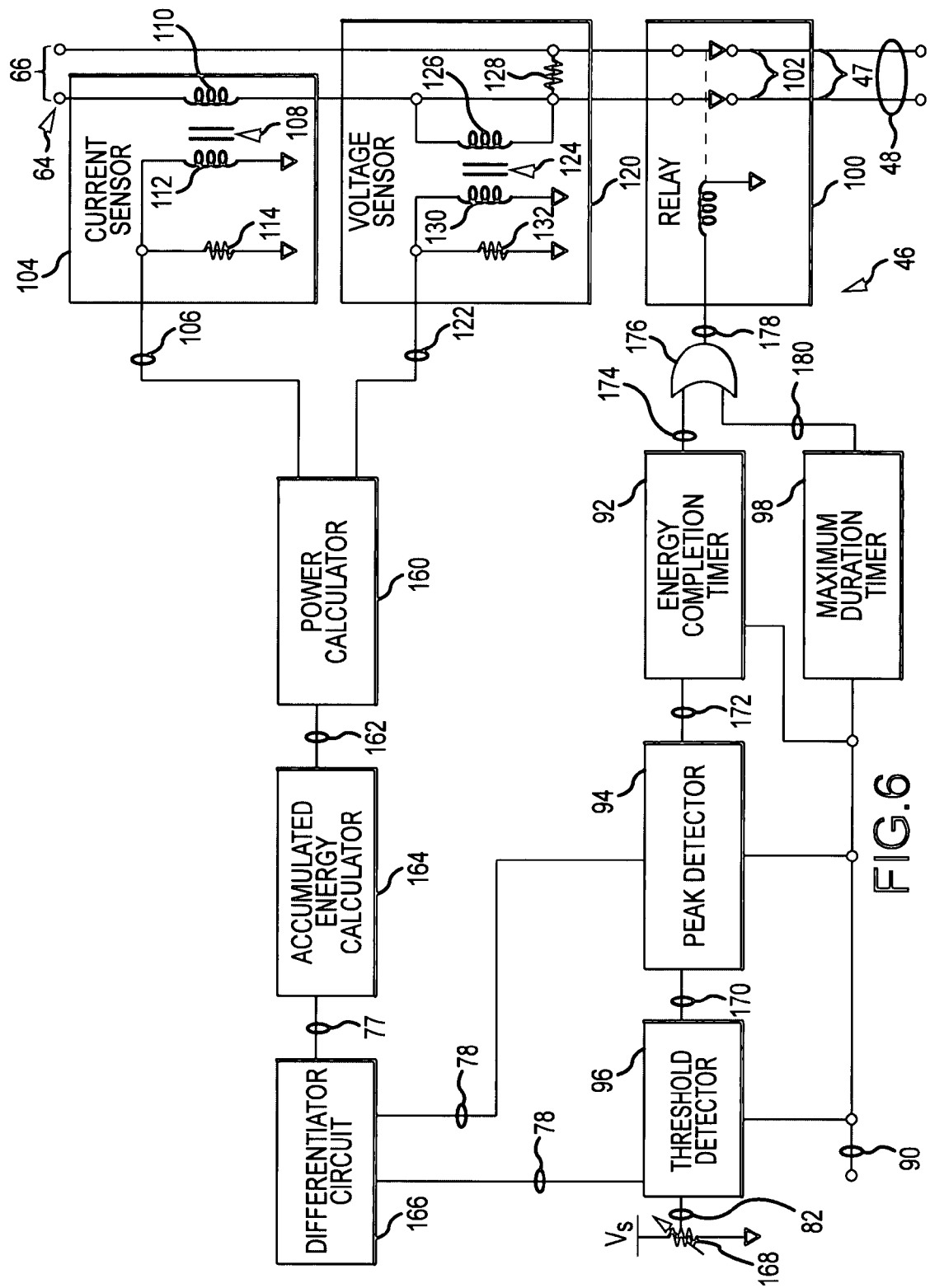
FIG. 6 is a block and schematic circuit diagram of components of a controller of the tissue sealing apparatus shown in FIG. 1.

The functional components of the controller 46 which achieve the energy monitoring and controlling functions are shown and described in conjunction with FIG. 6. The treatment cycle 68 (FIGS. 5a-5c) begins when the control switch 44 (FIG. 1) is closed or activated. Closing or activating the control switch 44 begins the treatment cycle 68. The control switch 44 delivers an activation signal 90 (FIG. 7) to the electrosurgical generator 42 and to the controller 46 (FIG. 1). The activation signal 90 causes the electrosurgical generator 42 to begin delivering the electrosurgical energy to the vessel 32 (FIG. 1).

In the controller 46 shown in FIG. 6, the activation signal 90 sets an initial state of an energy completion timer 92, a conventional peak detector 94, a conventional threshold detector 96 and a maximum treatment duration timer 98. A conventional relay 100 has normally closed switch contacts 102 which conduct the electrosurgical RF current 64 (FIG. 5) from the electrosurgical generator 42 through the controller 46 and the cable 48 to the jaws 40 of the handpiece 38, and from the jaws through the vessel 32 (FIG. 1).

A conventional current sensor 104 senses the RF current 64 (FIG. 5a) conducted through the controller 46 and produces a current sense signal 106 which is representative of the RF current 64. The current sensor 104 includes a current sense transformer 108 having a primary winding 110 through which the RF current 64 flows. A secondary winding 112 of the current sense transformer 108 develops a secondary current which is directly related to the magnitude and characteristics of the RF current 64. The secondary current from the secondary winding 112 is conducted through a resistor 114, and a voltage is developed across the resistor 114 which is related to the magnitude of the secondary current. The voltage across the resistor 114 creates the current sense signal 106 which corresponds to the value of the RF current 64 (FIG. 5a).

A conventional voltage sensor 120 senses the RF voltage 66 (FIG. 5b) applied through the controller 46 and produces a voltage sense signal 122 which is representative of the RF voltage 66 (FIG. 5b) applied to the compressed tissue. The voltage sensor 120 includes a voltage sense transformer 124 having a primary winding 126 connected in series with a resistor 128 which extends between the two conductors of the cable 48 which connect to the electrodes 50 (FIG. 1). Current flowing through the primary winding 126 and resistor 128 is directly related to the RF voltage 66 (FIG. 5b) across the electrodes 50 (FIG. 1). The voltage sense transformer 124 also includes a secondary winding 130 which develops a secondary current which is directly related to the current flowing through the primary winding 126, which is directly related to the magnitude and characteristics of the RF voltage 66 (FIG. 5b). The current from the secondary winding 130 flows through a resistor 132 which develops the voltage sense signal 122 that is directly related to the voltage across the electrodes 50 (FIG. 1).

A conventional power calculator 160 receives the current sense signal 106 and the voltage sense signal 122 and multiplies the signals 106 and 122 together to calculate the power conducted through the cable 48 to the compressed tissue. The power calculator 160 creates a power signal 162 that is directly related to the power that is delivered to the tissue through the electrodes 50 (FIG. 1).

A conventional accumulated energy calculator 164 receives the power signal 162 and calculates the accumulated energy delivered to the tissue during the tissue sealing treatment cycle 68 as represented by the accumulated energy curve 77 (FIG. 5c). The accumulated energy calculator 164 multiplies the power signal 162 with time to calculate the amount of accumulated energy that has been applied during the tissue sealing treatment cycle 68. The values of the accumulated energy are supplied at 77 and constitute the accumulated energy curve 77 (FIG. 5c). As shown in FIG. 5c, the longer the time that the treatment cycle 68 progresses, the greater the amount of the accumulated energy shown by the curve 77, since more energy is absorbed by the vessel 32.

A conventional differentiator circuit 166 shown in FIG. 6 receives the accumulated energy values from the accumulated energy calculator 164 and calculates second derivative values of the accumulated energy curve 77. The second derivative values are shown by, and therefore constitute, the second derivative curve 78 (FIG. 5c). The values of the second derivative curve 78 represent the rate of change of the rate of change (or acceleration) of the accumulated energy delivered to the vessel 32 (FIG. 1).

The threshold detector 96 receives the second derivative values 78 and a signal representative of the threshold value 82 (FIG. 5c), as shown in FIG. 6. The threshold value signal 82 is established by setting a potentiometer 168. The potentiometer 168, which constitutes a threshold level setting circuit, is connected as a voltage divider to vary the threshold signal 82, depending upon the adjustment of the potentiometer 168. The threshold value 82 is set to a level that exceeds the range of typical fluctuations of the second derivative curve 78 during the initial heating phase 72 (FIGS. 5a-5c), thereby eliminating the possibility that such fluctuations might falsely indicate conditions indicative of the desired precursor condition.

The threshold detector 96 compares the values of the second derivative curve 78 with the magnitude of the threshold value 82 (FIG. 5c). When the values of the second derivative curve 78 do not exceed the threshold value 82 (in the negative sense shown in FIG. 5c), the threshold detector 96 asserts a logical low peak detection enable signal 170. When the values of the second derivative curve 78 exceed (in a negative sense) the threshold value 82, the threshold detector 96 asserts a logical high peak detection enable signal 170 (FIG. 8). That assertion occurs at a time point 84 (FIGS. 5 and 8).

The peak detector 94 receives the peak detection enable signal 170 from the threshold detector 96 and the second derivative values representative of the second derivative curve 78 from the differentiator circuit 166. While the peak detection enable signal 170 is at a logical low state, the peak detector 94 does not examine the second derivative values. However, when the peak detection enable signal 170 is asserted at a logical high state at time 84 (FIGS. 5 and 8), indicating that the values of the second derivative curve 78 have exceeded the threshold value 82, the peak detector 94 begins to examine the second derivative values which form the second derivative curve 78 for their peak magnitude. When the magnitude of second derivative values reach a peak value (in the negative sense), which occurs at time point 86 (FIG. 5c), the peak detector 94 generates a logical high state precursor trigger signal 172 (FIG. 9). The peak detector 94 detects the peak amplitude (in a negative sense) of the second derivative values at the time point 86 (FIG. 5c) by employing conventional techniques such as determining when a slope of the second derivative values which form the derivative curve 78 becomes zero (which occurs at point 86). The peak value of the second derivative curve 78 constitutes the precursor fusion condition, which is detected at time point 86 (FIG. 5c).

In response to the assertion of the precursor trigger signal 172, the energy completion timer 92 commences counting the energy completion time 88 (FIGS. 5 and 9). The energy completion time 88 (FIGS. 5 and 9) is a predetermined fixed amount of time, which has been programmed or set into the energy completion timer 92. At the conclusion of counting the energy completion time 88, the timer 92 asserts a termination signal 174 at a logical high state (FIG. 10). The termination signal 174 is initially set to a logic low state by the activation signal 90.

An OR gate 176 receives the termination signal 174 from the energy completion timer 92. When the termination signal 174 is asserted at the logical high state, the OR gate 176 delivers a logic high level control signal 178 (FIG. 11) to the relay 100. The relay 100 responds to the logical high level relay control signal 178 by opening the normally-closed switch contacts 102, thereby terminating the flow of the RF current 64 (FIG. 5a) and voltage 66 (FIG. 5b) from the generator 42 to the handpiece 38 (FIG. 1). Opening the switch contacts 102 discontinues the delivery of electrical energy to the vessel 32 (FIG. 1) at the cycle termination time 76 (FIGS. 5a-5c and 11).

The energy completion timer 92 permits additional energy to be applied to the tissue after detection of the precursor fusion condition. The additional energy is necessary to obtain an effective seal of the compressed apposite sidewall portions of the tissue. Terminating the delivery of electrosurgical energy at the moment when the precursor fusion condition exists will not result in creating an effective seal. Terminating the application of heating energy immediately after the precursor fusion condition has occurred results in an insufficient number of collagen and elastin tissue fibers having loosened adequately enough to intertwine and fuse with one another. The additional energy is believed to be necessary to obtain the necessary loosening, fusing and intertwining of the relatively high denaturing temperature collagen and elastin fibers within the tissue to create an effective seal.

The additional energy added after the occurrence of the precursor fusion condition must be sufficient to drive off a substantial portion of the intracellular fluid within the cells of the tissue. Removing the intracellular fluid is believed to create the beneficial effect of locating tissue fibers within sufficiently close physical proximity to fuse and intertwine without the intracellular fluid interfering with the fusion and intertwining. Eliminating a substantial portion of the intracellular fluid is accomplished by delivering enough additional energy to vaporize the intracellular fluid. Typically the intracellular fluid is predominantly water. Consequently, the temperature of the intracellular fluid must be raised to or above 100° Celsius in order to vaporize that intracellular fluid.

The relay 100 also opens the switch contacts 102 in response to the assertion of a maximum cycle time duration signal 180 supplied by the maximum duration timer 98 (FIG. 6). The maximum duration timer 98 is set to count down a time that is longer than the duration of a normal treatment cycle 68 (FIGS. 5a-5c). If the countdown time set by the maximum duration timer 98 is reached, an unexpected condition will have occurred and the delivery of further electrosurgical energy under these conditions is not warranted. The maximum duration timer 98 assures that the electrical energy from the generator 42 (FIG. 1) is not applied for an excessively long amount of time.

The maximum duration timer 98 asserts the maximum duration signal 180 to the OR gate 176 at the expiration of the maximum duration time which has been set into the timer 98. The timer 98 begins counting in response to the assertion of the signal 90. The OR gate 176 responds to the assertion of the maximum duration signal 180 by asserting the logical high control signal 178 to the relay 100. The control signal 178 causes the switch contacts 102 to open and terminate the delivery of electrical power to the handpiece 38 (FIG. 1).

Figure 12:
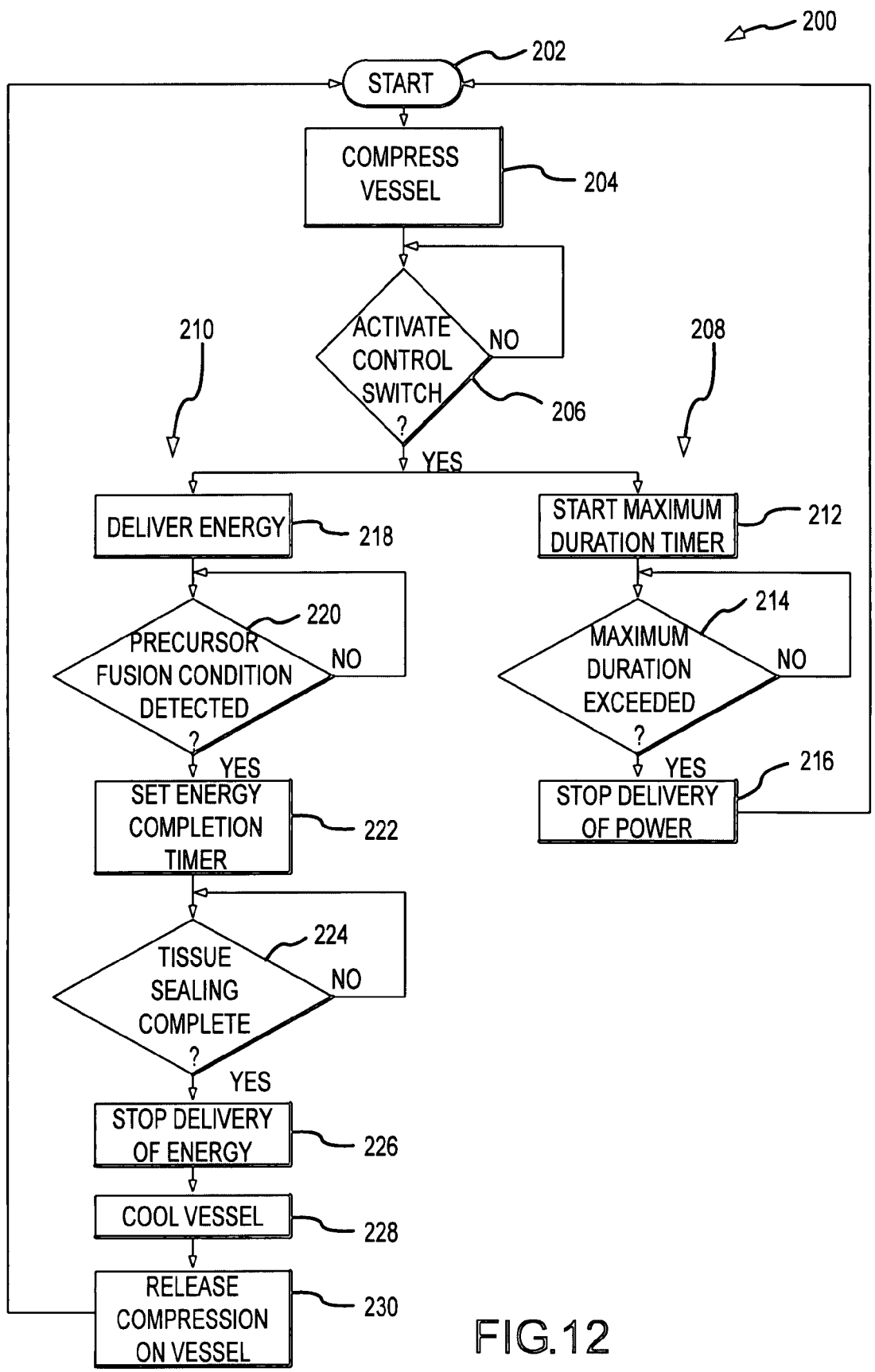
FIG. 12 is a flowchart illustrating aspects of a process flow executed by the tissue sealing apparatus shown in FIG. 1, when performing the tissue sealing treatment cycle, and also illustrating method aspects of the present invention.

The events involved in operating and using the coaptive sealing apparatus 30 (FIG. 1) during a treatment cycle 68 (FIGS. 5a-5c), and the events involved in performing coaptive tissue sealing, are summarized in a sequence 200 shown in FIG. 12. The sequence 200 begins at 202. The vessel 32 is compressed (FIGS. 2-4) at 204 by use of the handpiece 38 (FIG. 1). Next, it is determined at 206 whether the control switch 44 (FIG. 1) has been activated. If the determination at 206 is negative, a wait loop is executed until the control switch 44 is activated. Activation of the control switch 44 is recognized by an affirmative determination at 206. After this point, the sequence 200 diverges into two simultaneously-executed sub-series of events 208 and 210. The sub-series of events 208 involves limiting the maximum time duration of the treatment cycle 68 (FIGS. 5a-5c), and the sub-series of events 210 involves the normal execution of a treatment cycle 68 for fusing or sealing tissue.

The sub-series of events 208 commences at 212 with starting the maximum duration timer 98 (FIG. 6) to begin its countdown. Next, a determination is made at 214 as to whether the maximum time duration set in the maximum duration timer 98 has been reached. A wait loop is executed as indicated by the negative determination at 214 until the maximum time duration has been reached or counted down to zero. If the maximum time duration is reached, as indicated by an affirmative determination at 214, the delivery of electrical energy is terminated at 216, as a result of the timer 98 delivering the maximum duration signal 132 (FIG. 6) to open the switch contacts 102 of the relay 100 (FIG. 6). As discussed previously, a normal treatment cycle 68 (FIGS. 5a-5c) is typically completed well before the maximum duration timer 98 (FIG. 6) counts down to zero and terminates the delivery of electrical energy from the generator 42 to the handpiece 38

(FIG. 1). The sub-series of events 208 comes into play only under conditions when the normal tissue fusion fails for some unexpected reason during the treatment cycle 68 (FIGS. 5a-5c). Normally, the normal treatment cycle 68 (FIGS. 5a-5c) is represented by the sub-series of events 210 and will be executed as intended, and consequently, the sub-series of events 208 will not be completed as just described.

The sub-series of events 210 relates to the execution of a normal treatment cycle 68 (FIGS. 5a-5c). The execution of a normal treatment cycle commences with the delivery of electrosurgical energy at 218. After the energy delivery begins, a determination is made at 220 as to whether the precursor fusion condition has been detected. The precursor fusion condition is detected by determining whether the value of the derivative curve 78 (FIG. 5c) has surpassed the threshold value 82 (FIG. 5c) and reached a peak value (as previously discussed in conjunction with FIGS. 5, 6 and 9). If the precursor fusion condition has not been detected, the determination at 220 is negative and a wait loop is executed until the precursor fusion condition has been detected as indicated by an affirmative determination at 220.

Detection of the precursor fusion condition, indicated by an affirmative determination at 220, triggers the energy completion timer 92 (FIG. 6) at 222 to begin counting the energy completion time 88 (FIGS. 5 and 10). Next, a determination is made at 224 as to whether the tissue sealing is complete as represented by the energy completion timer 92 (FIG. 6) counting down to zero. Until the tissue sealing is complete and the energy completion timer has counted down to zero, a wait loop is executed. The wait loop is represented by a negative determination at 224. When the determination at 224 is affirmative, indicating that the electrosurgical generator 42 (FIG. 1) has applied an adequate amount of electrical energy to the tissue for an effective seal, the sequence advances to 226, where the delivery of the electrosurgical energy is terminated (FIG. 10). Under these circumstances, the switch contacts 102 of the relay 100 (FIG. 6) are opened, and the delivery of energy from the electrosurgical generator 42 is terminated, despite the fact that the control switch 44 (FIG. 1) may remain activated or closed.

After terminating the power delivery at 226, the opposed portions of the sidewall 36 of the tissue (FIGS. 3 and 4) cool at 228, and the tissue fibers intertwine and fuse together in a manner which resists separation. The cooling can occur almost instantaneously depending upon the thickness and surface area of the tissue and other factors. The cooling may also be sufficient to cause the fibers to intertwine enough to hold the apposite side wall portions of the tissue together, even though the temperature of the vessel may not have reached a normal level. The cooling may occur so quickly that the compression force or pressure on the sealed apposite portions of the sidewall 36 may be released almost immediately after the delivery of energy is stopped. The compression force or pressure on the tissue is released at 230 by opening the jaws 40 after having disengaged the teeth 60 of the tabs 58 (FIG. 1). Thereafter, the sequence 200 returns to 202 to await the beginning of another treatment cycle 68 (FIGS. 5a-5c), which is instituted by again activating the control switch 44 (FIG. 1).

The present invention can be implemented by using a ConMed System 5000 electrosurgical generator as the electrosurgical generator 42 (FIG. 1) and by using either a standard handheld Valleylab Ligasure handpiece or a laparoscopic ValleyLab Ligasure handpiece as the handpiece 38 (FIG. 1). The ConMed System 5000 electrosurgical generator is operated in a fluid macro bipolar mode. The advantage of using the fluid macro bipolar mode is that it has the capability of delivering a relatively high amount of power into a relatively low impedance tissue. This characteristic delivers enough electrical energy into the compressed apposite portions of the sidewall 36 to heat the sidewall portions rapidly during the initial heating phase 72 (FIGS. 5a-5c). The fluid bipolar mode was originally intended to be used in arthroscopic surgery where the surgical site is totally immersed in water or saline. Because of the high conductivity and therefore low impedance of the water or saline, the boosted power capacity and lower internal source impedance in the fluid bipolar mode create an added capability to quickly deliver energy, which is useful in the present invention to quickly heat the compressed apposite sidewall portions of the tissue. Less thermal spread to the adjoining tissues occurs compared to that resulting from using a standard electrosurgical generator operated in the conventional cutting or coagulation mode of power delivery. The higher rate of energy delivery is accomplished in part by more closely matching the source impedance of the electrosurgical generator with the load impedance of the compressed apposite portions of the sidewall 36, thereby enhancing the energy transfer capability of the electrosurgical generator into low impedance tissue.

The ConMed System 5000 electrosurgical generator is set to deliver 90 watts of electrosurgical energy when used with the standard handheld Valleylab Ligasure handpiece. The ConMed System 5000 electrosurgical generator is set to deliver 70 watts of electrosurgical energy when used with a 5 mm laparoscopic Valleylab Ligasure handpiece. The threshold value 82 (FIG. 5c) is established when the current envelope (FIG. 5a) falls below 1.8 amps represented by the value 82 on FIG. 5c, although other values could also be used depending on the generator, handpiece and other factors. The energy completion time 88 (FIGS. 5a-5c) is set in the energy completion timer 92 (FIG. 6) at approximately 0.86 seconds, although values from approximately 0.6 to 1.2 seconds are also considered acceptable. In the specific embodiment of the tissue sealing apparatus 30, the maximum duration timer 98 (FIG. 6) is set with a maximum duration time of approximately 12 seconds, which is at least two times greater than the normal tissue sealing cycle time.

Using the embodiment of the invention described in the immediately preceding paragraph, the complete tissue sealing cycle time for arteries and veins is about 3 to 5 seconds. However, the accepted practice of using the popular prior art tissue sealing device is to perform four separate seals, with two of the seals overlapped and with each pair of overlapped seals spaced longitudinally from one another along the length of the vessel, making total sealing times in the neighborhood of approximately 20 seconds commonplace. Tests performed with the embodiment of the invention described above have demonstrated that a single seal is more effective than multiple seals with 100% overlap. Mean burst pressures of a single seal on a vessel accomplished by use of the above described apparatus are equal or somewhat greater than the mean burst pressures of multiple seals on a comparable vessel accomplished by use of the popular prior art tissue sealing device.

Using the above-described apparatus resulted in transferring an average of approximately 35 watts of electrical power to the vessel, which is typically considerably less than the total energy delivered for sealing a comparable vessel by the popular prior art tissue sealing device. Applying less energy to achieve the same or better seal burst pressures results in less tissue damage. Healing time is shortened because of the lesser tissue damage.

The values for the threshold value 82 and the energy completion time 88 (FIGS. 5a-5c) were established relative to the apparatus described above. These values may need to be adjusted for other types of electrosurgical generators depending on their output energy delivery characteristics, their source impedances, their real or apparent power regulation characteristics, the impedances of the handpieces used, and the types of tissue which are sealed, among other things. The electrosurgical generator should have the capability of delivering relatively significant amounts of power in a relatively short time into relatively low impedances, such as those represented by the compressed apposite portions of the sidewall 36 of the tissue to be sealed.

As an alternative to detecting the peak value of the second derivative curve 78 at time 86 (FIGS. 5a-5c), the precursor tissue fusion condition could be detected when the second derivative values represented by the derivative curve 78 exceed (in a negative sense as illustrated) the threshold value 82 (FIG. 5c). Under this circumstance, the completion time will need to be adjusted to a slightly greater value compared to that value when the precursor tissue fusion condition is determined from the peak value of the second derivative curve 78 (FIG. 5c).

The sealing capability by the present invention is obtained without resorting to complicated and expensive feedback power controls and impedance-related sensing techniques, as are prevalently used in prior art tissue sealing devices, and provides much better capability than human estimates of the appropriate time for energy delivery for tissue sealing. Indeed, experiments have shown that the RMS impedance of the tissue varies considerably at the time of occurrence of the above-described precursor fusion condition. The range of tissue impedance values at the precursor condition indicates that tissue impedance values do not correlate to the precursor condition, and therefore using an impedance value for the precursor fusion condition is not a suitable replacement for using the peak of the second derivative values as the precursor fusion condition in accordance with the present invention. Many other advantages and improvements will be apparent upon gaining a full appreciation for the present invention.

A presently preferred embodiment of the invention and many of its improvements have been described above with a degree of particularity. The description is of the preferred example of implementing the invention, and is not necessarily intended to limit the scope of the invention. The scope of the invention is defined by the following claims.

The invention claimed:

1. A method of coaptively sealing a sidewall of biological tissue which surrounds and defines an opening in the tissue to occlude the opening, the tissue of the sidewall comprising biological fibers, the method comprising:
   compressing portions of the sidewall in apposition to occlude the opening;
   applying sufficient energy to the compressed apposed sidewall portions to cause the fibers of the compressed apposed sidewall portions to intertwine and fuse with one another to a sufficient degree to hold the apposed sidewall portions together permanently and to occlude the opening permanently;
   applying the energy by conducting radio frequency (RF) energy through the compressed apposed portions of the sidewall;
   determining values of the cumulative amount of RF energy applied to the sidewall portions;
   mathematically differentiating the values of the cumulative energy applied to create derivative values of the cumulative energy applied to the compressed apposite sidewall portions;
   detecting a precursor fusion condition from the derivative values while applying the energy to the compressed apposite sidewall portions and before sufficient energy has been applied to cause the fibers to intertwine and fuse to the sufficient degree; and
   terminating the application of energy in a time-delayed relationship to the detection of the precursor fusion condition when the sufficient degree of energy has been conducted to the compressed apposed sidewall portions to intertwine and fuse the fibers to hold the apposed sidewall portions together permanently and to occlude the opening permanently.

2. A method as defined in claim 1, further comprising:
   terminating the application of energy after the expiration of a fixed time duration after detecting the precursor fusion condition.

3. A method as defined in claim 1, further comprising:
   mathematically differentiating the values of the cumulative energy applied to create second derivative values of the cumulative energy applied; and
   detecting the precursor fusion condition at a peak of the second derivative values.

4. A method as defined in claim 3, further comprising:
   terminating the application of energy at a predetermined energy completion time after the precursor fusion condition has been detected.

5. A method as defined in claim 4, wherein the energy completion time is in the range of 0.6 to 1.2 seconds.

6. A method as defined in claim 4, wherein the energy completion time is approximately 0.86 seconds.

7. A method as defined in claim 1, further comprising:
   mathematically differentiating the values of the cumulative energy applied to create second derivative values of the cumulative energy applied;
   comparing the second derivative values to a predetermined threshold value; and
   detecting the precursor fusion condition after second derivative values exceed the predetermined threshold value.

8. A method as defined in claim 7, further comprising:
   terminating the application of energy at a predetermined energy completion time after the precursor fusion condition has been detected.

9. A method as defined in claim 8, further comprising:
   mathematically differentiating the values of the cumulative energy applied to create second derivative values of the cumulative energy applied; and
   detecting the precursor fusion condition upon the occurrence of a peak of the second derivative values.

10. A tissue sealing apparatus for coaptively sealing a sidewall of biological tissue which surrounds and defines an opening in the tissue to occlude the opening, the tissue of the sidewall comprising biological fibers, the apparatus comprising:
   a handpiece having jaws movable to close on and compress portions of the sidewall in apposition to one another to occlude the opening;
   an electrical energy generator connected to the handpiece to deliver high frequency energy to the jaws, the generator delivering sufficient high frequency energy from the jaws through the compressed apposed sidewall portions to cause the fibers of the compressed apposed sidewall portions to intertwine and fuse with one another to a sufficient degree to hold the apposed sidewall portions together permanently and to occlude the opening permanently; and
   a controller connected to the generator and the jaws to control the delivery of the high frequency energy from the generator to the jaws, the controller including a switch, a precursor detector and an energy completion timer;

the switch controlling delivery of high frequency energy from the generator to the jaws, the switch movable between opened and closed positions in response to a control signal applied to the switch, the closed position of the switch conducting the high frequency energy from the generator to the jaws, the opened position of the switch terminating the conduction of the high frequency energy from the generator to the jaws;

the precursor detector sensing the high frequency energy conducted from the generator through the switch to the jaws, the precursor detector establishing values of the cumulative amount of high frequency energy applied to the compressed apposite sidewall portions, the precursor detector mathematically differentiating values of the cumulative energy applied to create derivative values of the cumulative energy applied while the high frequency energy is conducted from the generator through the switch to the jaws and through the compressed apposite sidewall portions, the precursor detector determining a precursor fusion condition from the derivative values while the high frequency energy is applied to the compressed apposite sidewall portions and before sufficient energy has been applied to cause the fibers to intertwine and fuse to the sufficient degree, the precursor detector delivering a precursor trigger signal upon detecting the precursor fusion condition from the derivative values; and the energy completion timer connected to the precursor detector and to the switch and receptive of the precursor trigger signal, the energy completion timer asserting a termination signal as the control signal to the switch to cause the switch to move from the closed position to the opened position upon the expiration of a time after the assertion of the precursor trigger signal at which sufficient energy has been applied to the compressed apposed sidewall portions to cause the fibers to intertwine and fuse with one another to the sufficient degree.

11. A tissue sealing apparatus as defined in claim 10, wherein:
the energy completion timer asserts the termination signal upon the expiration of a predetermined fixed time after the assertion of the precursor trigger signal.

12. A tissue sealing apparatus as defined in claim 10, wherein:
the precursor detector mathematically differentiates the values of the cumulative energy applied to create second derivative values of the cumulative energy applied; and
the precursor detector asserts the precursor trigger signal upon detecting a peak of the second derivative values.

13. A tissue sealing apparatus as defined in claim 10, wherein:
the precursor detector mathematically differentiates the values of the cumulative energy applied to create second derivative values of the cumulative energy applied; and
the precursor detector compares the second derivative values to a predetermined threshold value and asserts the precursor trigger signal after the second derivative values exceed the predetermined threshold value.

14. A tissue sealing apparatus as defined in claim 13, wherein:
the precursor detector asserts the precursor trigger signal upon detecting a peak of the second derivative values.

15. A tissue sealing apparatus as defined in claim 14, wherein:
the energy completion timer asserts the termination signal upon the expiration of a predetermined fixed time after the assertion of the precursor trigger signal.

16. A tissue sealing apparatus as defined in claim 15, wherein the predetermined fixed time is in the range of 0.6 to 1.2 seconds.

17. A tissue sealing apparatus as defined in claim 16, wherein the predetermined fixed time is approximately 0.86 seconds.

18. A tissue sealing apparatus as defined in claim 11, wherein:
the precursor detector mathematically differentiates the values of the cumulative energy applied to create second derivative values of the cumulative energy applied.

19. A controller to connect an electrosurgical generator and to a tissue sealing handpiece to create a tissue sealing apparatus for coaptively sealing a sidewall of biological tissue which surrounds and defines an opening in the tissue to occlude the opening, the tissue of the sidewall comprising biological fibers, the handpiece having jaws movable to close on and compress portions of the sidewall in apposition to one another to occlude the opening, the electrosurgical generator delivering radio frequency (RF) energy to be conducted from the jaws through the compressed apposed sidewall portions, the controller comprising:

a switch which controls delivery of the RF energy from the generator to the jaws, the switch movable between opened and closed positions in response to a control signal applied to the switch, the closed position of the switch conducting the RF energy from the generator to the jaws, the opened position of the switch terminating the conduction of the RF energy from the generator to the jaws;

a precursor detector which senses the RF energy conducted from the generator through the switch to the jaws and through the compressed apposite sidewall portions, the precursor detector establishing values of the cumulative amount of RF energy applied to the compressed apposite sidewall portions, the precursor detector mathematically differentiating values of the cumulative energy applied to create derivative values of the cumulative energy applied while the RF energy is conducted from the generator through the switch to the jaws and through the compressed apposite sidewall portions, the precursor detector determining a precursor fusion condition from the derivative values while the RF energy is applied to the compressed apposite sidewall portions and before sufficient energy has been applied to cause the fibers to intertwine and to fuse to a sufficient degree for occluding the opening permanently, the precursor detector delivering a precursor trigger signal upon detecting the precursor fusion condition from the derivative values; and an energy completion timer connected to the precursor detector and to the switch and receptive of the precursor trigger signal, the energy completion timer asserting a termination signal as the control signal to cause the switch to move from the closed position to the opened position upon the expiration of a time after the assertion of the precursor trigger signal at which sufficient RF energy has been applied to the compressed apposed sidewall portions to cause the fibers to intertwine and fuse with one another to a sufficient degree to hold the apposed sidewall portions together permanently and occlude the opening permanently.

20. A controller as defined in claim 19, wherein:

the energy completion timer asserts the termination signal upon the expiration of a predetermined fixed time after the assertion of the precursor trigger signal.

21. A controller as defined in claim 20, wherein:

the precursor detector mathematically differentiates the values of the cumulative energy applied to create second derivative values of the cumulative energy applied; and the precursor detector asserts the precursor trigger signal upon detecting a peak of the second derivative values.

22. A controller as defined in claim 21, wherein:

the precursor detector further compares the derivative to a predetermined threshold value and asserts the precursor trigger signal after the second derivative values exceed the predetermined threshold value.

23. A controller as defined in claim 19, further comprising:

terminating the application of energy at a predetermined energy completion time after the precursor fusion condition has been detected.

* * * * *